US 8,098,915 B2

(12) United States Patent
Schneider et al.

(10) Patent No.: US 8,098,915 B2
(45) Date of Patent: Jan. 17, 2012

(54) LONGITUDINAL PULSE WAVE ARRAY

(75) Inventors: John K. Schneider, Snyder, NY (US);
Jack C. Kitchens, Tonawanda, NY (US)

(73) Assignee: Ultra-Scan Corporation, Amherst, NY (US)

(*) Notice: Subject to any disclaimer, the term of this patent is extended or adjusted under 35 U.S.C. 154(b) by 0 days.

(21) Appl. No.: 12/554,644

(22) Filed: Sep. 4, 2009

(65) Prior Publication Data
US 2010/0052478 A1  Mar. 4, 2010

Related U.S. Application Data

(63) Continuation-in-part of application No. 12/110,876, filed on Apr. 28, 2008, which is a continuation-in-part of application No. 11/754,131, filed on May 25, 2007.

(60) Provisional application No. 60/803,150, filed on May 25, 2006, provisional application No. 60/822,087, filed on Aug. 11, 2006, provisional application No. 60/914,203, filed on Apr. 26, 2007.

(51) Int. Cl.
*G06K 9/00* (2006.01)
(52) U.S. Cl. ....................................................... 382/128
(58) Field of Classification Search .................. 382/123, 382/128; 600/437, 463
See application file for complete search history.

(56) References Cited

U.S. PATENT DOCUMENTS

| 3,778,756 | A | | 12/1973 | Houston et al. |
| 4,211,949 | A | * | 7/1980 | Brisken et al. ............... 310/322 |
| 4,385,831 | A | | 5/1983 | Ruell |
| 4,434,799 | A | | 3/1984 | Taenzer |
| 4,730,495 | A | | 3/1988 | Green |
| 5,768,010 | A | | 6/1998 | Iwamoto |
| 6,445,109 | B2 | | 9/2002 | Percin et al. |
| 6,974,417 | B2 | | 12/2005 | Lockwood et al. |
| 7,037,268 | B1 | | 5/2006 | Sleva et al. |
| 7,382,688 | B2 | | 6/2008 | Miyazaki et al. |
| 2005/0041559 | A1 | | 2/2005 | Hendriks et al. |
| 2005/0163353 | A1 | | 7/2005 | Schneider et al. |

FOREIGN PATENT DOCUMENTS

WO    WO 2006/042144 A2    4/2006

* cited by examiner

*Primary Examiner* — Daniel Mariam
*Assistant Examiner* — Elisa Rice
(74) *Attorney, Agent, or Firm* — Hodgson Russ LLP

(57) ABSTRACT

An acoustic pulse array is described. The pulse array can include a plane wave pulse generator having a first side from which a first wave emanates, and a second side from which a second wave emanates. A first waveguide array can be attached to the generator on the first side of the generator, and a second waveguide array can be attached to a second side of the generator. One or more of the waveguides can be attached to the generator so as to orient the waveguide to transmit wave pulses in a direction that is substantially perpendicular to the generator.

9 Claims, 5 Drawing Sheets

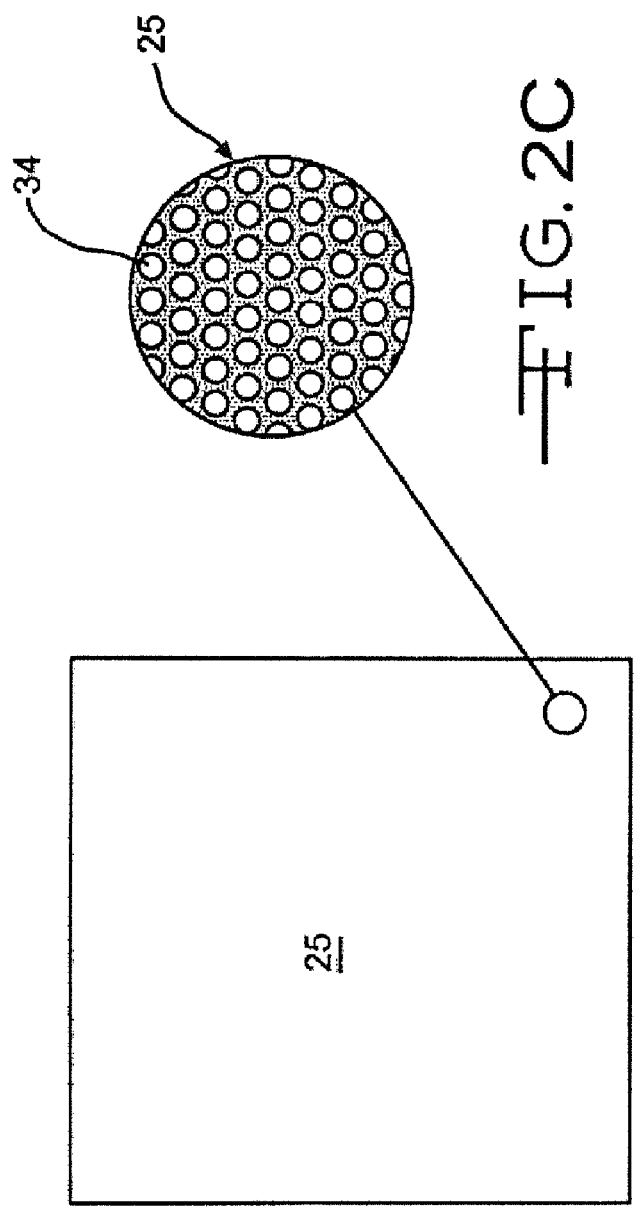
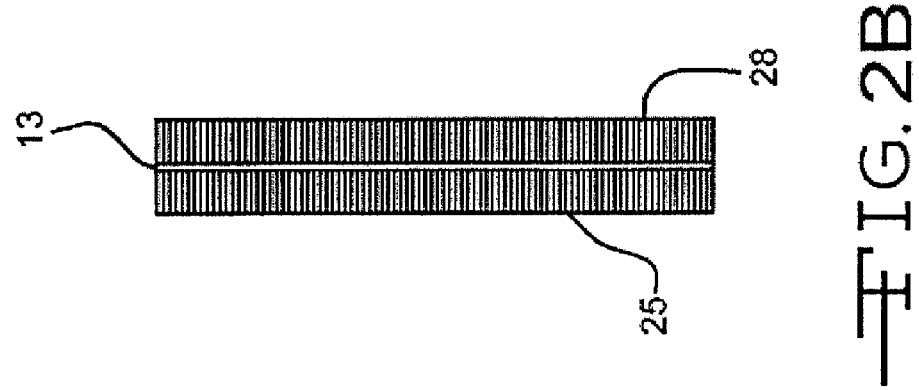

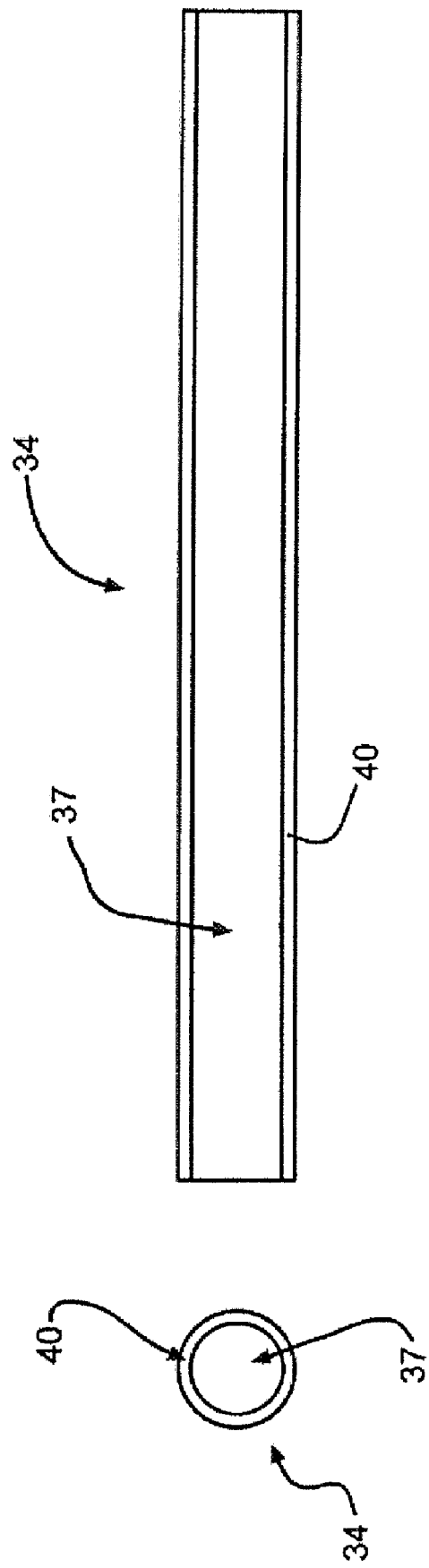

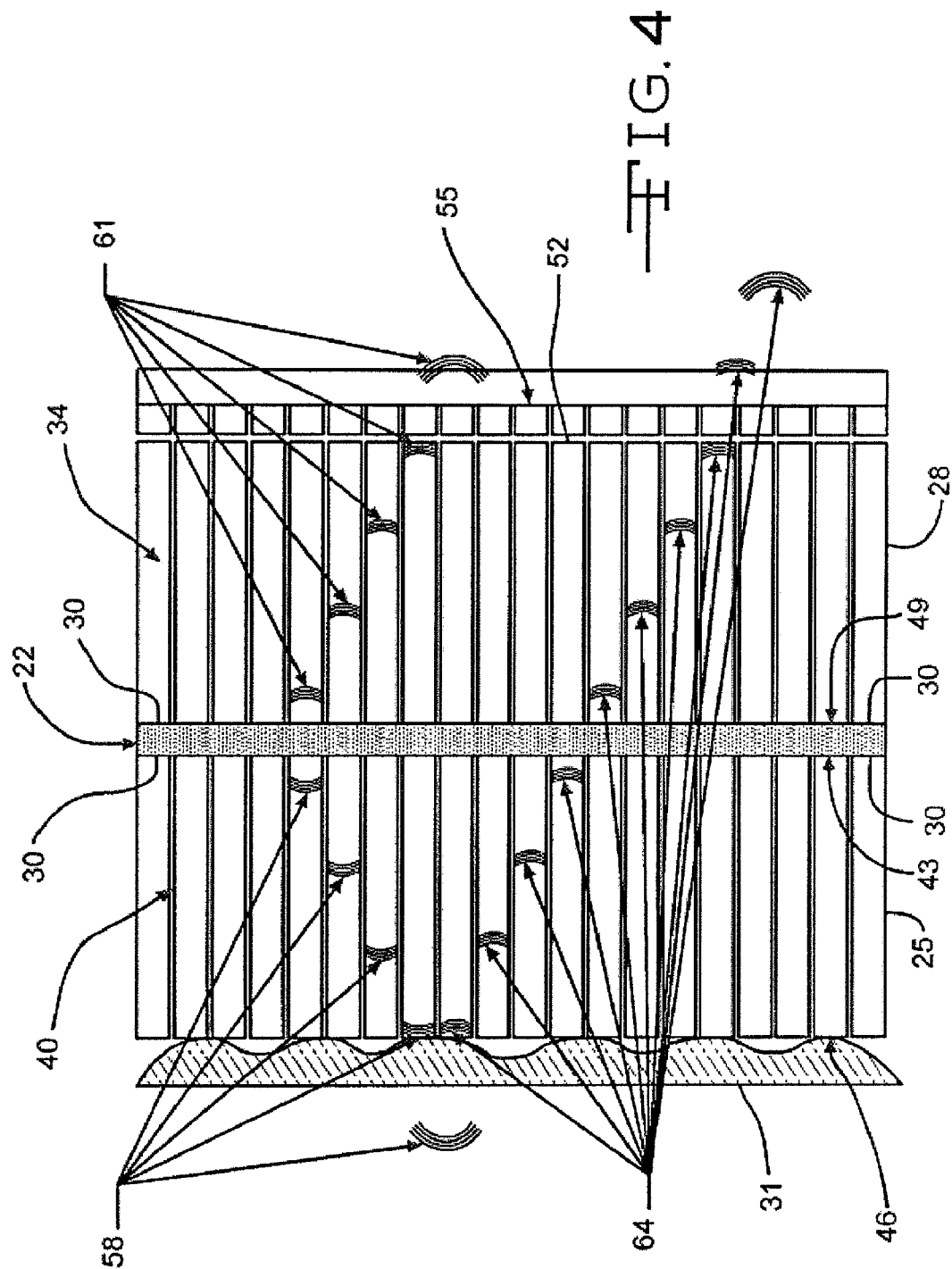

LONGITUDINAL PULSE WAVE ARRAY

CROSS-REFERENCE TO RELATED APPLICATIONS

This application is a continuation-in-part of U.S. patent application Ser. No. 12/110,876, which was filed Apr. 28, 2008, and this application claims the benefit of priority to U.S. patent application Ser. No. 12/110,876. Ser. No. 12/110,876 is a continuation-in-part of U.S. patent application Ser. No. 11/754,131, which was filed on May 25, 2007. The 12/110,876 and 11/754,131 applications each claim the benefit of priority to U.S. provisional patent application Ser. No. 60/803,150, which was filed on May 25, 2006, and to U.S. provisional patent application Ser. No. 60/822,087, which was filed on Aug. 11, 2006 and to U.S. provisional patent application Ser. No. 60/914,203, which was filed on Apr. 26, 2007. This application claims the benefit of 60/803,150, 60/822,087, and 60/914,203.

FIELD OF THE INVENTION

This disclosure relates to an acoustic pulse array and, more specifically, to a flat panel acoustic pulse array employing piezoelectric pulse generating means. In this document the term "acoustic" is used to refer to a longitudinal wave, such as an ultrasound wave, even though the wave may not be audible.

BACKGROUND

Existing acoustic imaging systems make use of single-pixel-scanning techniques and phased array techniques. These techniques result in imaging systems that are bulky and cumbersome.

BRIEF SUMMARY OF THE INVENTION

In one implementation, an acoustic pulse array can include a plane wave pulse generator (sometimes referred to herein as an "acoustic wave generator") having a first side from which a first wave emanates, and a second side from which a second wave emanates. A first waveguide array can be attached to the generator on the first side of the generator, and a second waveguide array can be attached to a second side of the generator. One or more of the waveguides can be attached to the generator so as to orient the waveguide to transmit wave pulses in a direction that is substantially perpendicular to the acoustic wave generator.

The acoustic wave generator can include a piezoelectric film and two electrodes. A first one of the electrodes can be bonded to a first side of the film, and can substantially cover a first side of the film. A second one of the electrodes can be bonded to a second side of the film and can substantially cover a second side of the film. The first waveguide array can be attached to the first electrode, and/or the second waveguide array can be attached to the second electrode.

Each waveguide array can be comprised of a plurality of waveguides, each waveguide having a core material and cladding material. Within a waveguide array, the cladding material of one waveguide can be fused with the cladding material of another waveguide. The core and cladding material can be selected so that acoustic energy can be conveyed using internal reflection within a waveguide.

An acoustic pulse array can be used to produce and send acoustic energy toward a target object where some of the energy is reflected by the target object. The reflected acoustic energy can be guided by the waveguide arrays to a detector, which can have an appropriate number of acoustic energy receiving elements. In doing so, crosstalk between waveguides in an array, signal loss from a waveguide array, and interference from outside the waveguide array can be minimized. At the detector, the acoustic energy can be converted to an electric signal, and that electric signal can be used to create a grayscale image.

BRIEF DESCRIPTION OF THE SEVERAL VIEWS OF THE DRAWINGS

For a fuller understanding of the nature and objects of the invention, reference should be made to the accompanying drawings and the subsequent description. The invention will now be described by way of non-limiting examples, with reference to the attached drawings and diagrams in which:

FIG. 2A is a top view of an acoustic pulse array that is in keeping with the invention;

FIG. 2B is a side view of the acoustic pulse array depicted in FIG. 2A;

FIG. 2C is an enlarged view of a portion of the acoustic pulse array depicted in FIG. 2A;

FIG. 3A shows a side-view of an acoustic waveguide;

FIG. 3B shows an end-view of the acoustic waveguide depicted in FIG. 3A;

FIG. 4 is a schematic representation showing the travel of a single element pulse at different times and different fibers within the acoustic pulse array. Also shown are a target object and an acoustic detector array that can receive the acoustic pulses; FIG. 5 depicts the scanner in an assembled form and in an exploded form.

DETAILED DESCRIPTION OF THE INVENTION

Figure 1:
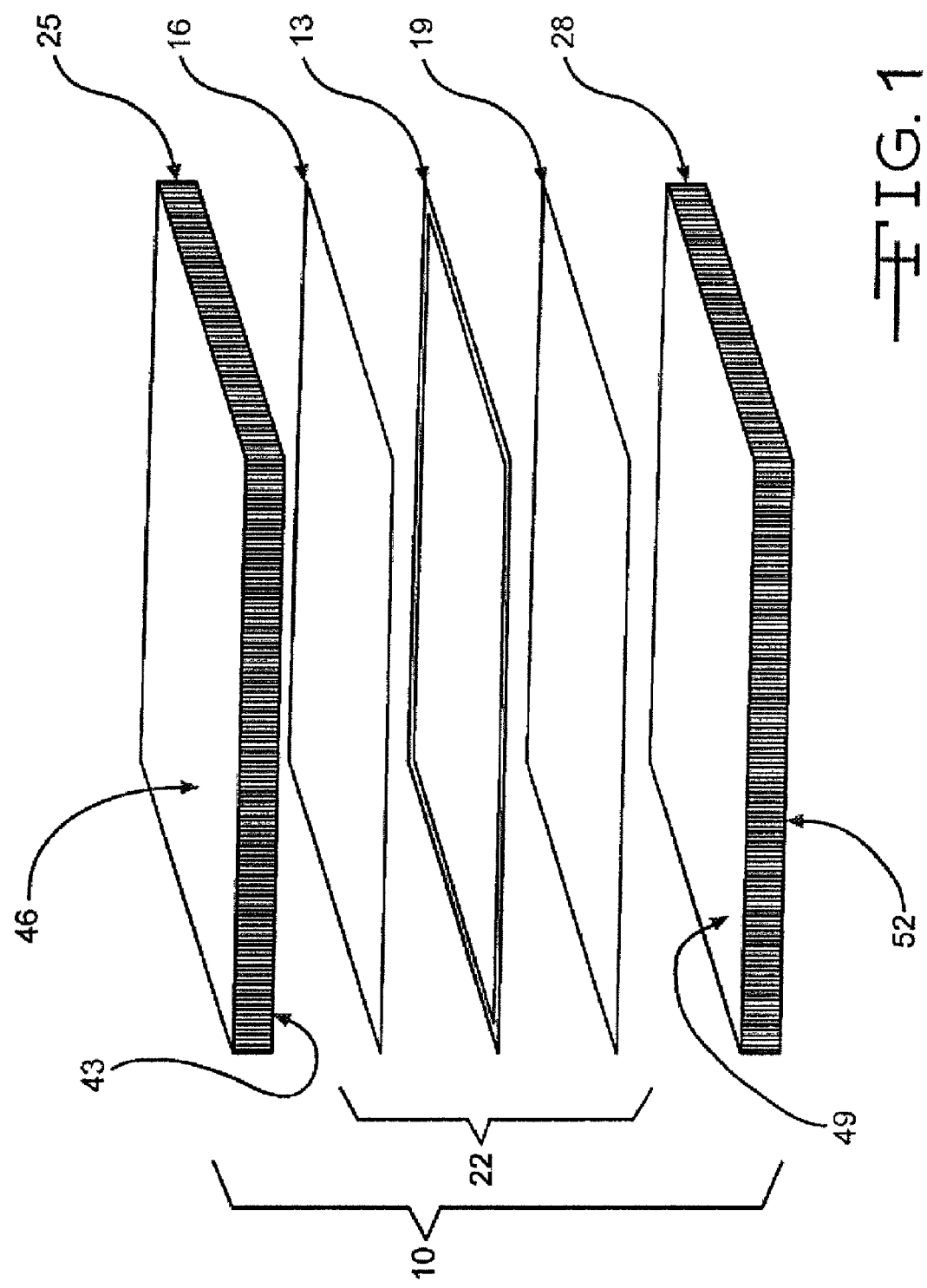
FIG. 1 is an exploded perspective view of an acoustic pulse array that is in keeping with the invention.

FIG. 1 shows components of an acoustic pulse array 10. A piezoelectric film 13 can be positioned between a first electrode 16 and a second electrode 19. The piezoelectric film 13 can be polyvinylidenefluoride ("PVDF") polymer or polyvinylidene fluoride trifluoroethylene ("PVDF-TrFE") and the electrodes 16, 19 can be metalized films of silver, indium-tin-oxide, chrome-gold, gold or some other conductive material. The electrodes 16, 19 can be vacuum sputtered to the piezoelectric film 13. The combination of the piezoelectric film 13 and the electrodes 16, 19 is referred to herein as acoustic wave generator ("AWG") 22. The AWG 22 can be positioned between a first waveguide array 25 and a second waveguide array 28. Each waveguide array 25, 28 has the ability to convey acoustic energy from one side of the array to another side of the array. The waveguide arrays 25, 28 can be attached to the AWG 22 by an adhesive 30, such as epoxy or cyanoacrylate, residing between the waveguide arrays 25, 28 and their respective electrodes 16, 19, or by squeezing the AWG 22 together by simple compression or clamping.

By placing the AWG 22 between two waveguide arrays 25, 28, the AWG 22 (and particularly the piezoelectric film 13) is reinforced. Without such reinforcement, creation of the pulses can be unbalanced, and the AWG 22 will create a signal having a frequency that is half the frequency at which the AWG 22 is oscillating. For example, if the AWG 22 is attached to only a single waveguide array and the film 13 is oscillated at 30 MHz, the frequency of the signal emanating toward a target object 31 would be 15 MHz. But, by attaching the AWG 22 to two waveguide arrays 25, 28, the piezoelectric film 13 will produce a 30 MHz signal emanating toward a target object 31.

Each waveguide array 25, 28 can be comprised of a plurality of waveguides 34. FIGS. 2A, 2B and 2C depict a waveguide array, and FIGS. 3A and 3B depict a waveguide 34. Each waveguide 34 can be thought of as a fiber having a core material 37 and a cladding material 40. The core material 37 and cladding material 40 are selected to have different abilities to transmit acoustic waves. The core material 37 is selected to have an acoustic wave transmission velocity that is substantially higher than the acoustic wave transmission velocity in the cladding material 40. For example, the core can be polystyrene and the cladding can be optical grade polymethylmethacrylate. As such, an acoustic wave traveling through the acoustic waveguide is conducted by means of total internal reflection at the interface of the two different materials 37, 40. Taken together, these two materials 37, 40 function as a coherent acoustic waveguide, and a plurality of such waveguides 34 can be combined to form a plate of waveguides, i.e., an array 25, 28 of acoustic waveguide elements.

With reference to FIG. 4, when the AWG 22 issues an ultrasonic pulse of energy, the first waveguide array 25 conducts ultrasonic energy from a first side 43 of the first waveguide array 25, through the individual acoustic waveguide elements 34 to the second side 46 of the first waveguide array 25. When the ultrasonic energy reaches the second side 46 of the first waveguide array 25, the energy is provided to a target object 31, such as a finger having a fingerprint. Some of the energy can continue on or be scattered and the balance will be reflected back through the fibers 34 of the first waveguide array 25, where the reflected energy passes through the AWG 22 and enters the second waveguide array 28. The reflected ultrasonic energy will be conducted from a first side 49 of the second waveguide array 28, via the waveguide elements 34 of the second waveguide array 28, to a second side 52 of the second waveguide array 28. At this point the reflected acoustic energy being emitted from the second side 52 of the second waveguide array 28 can be detected by a suitable acoustic detector 55 that can be fixed relative to the acoustic pulse array 10.

It should be noted that some of the ultrasonic energy produced by the AWG 22 will pass into the waveguide arrays 25, 28, but not into the cores 37 of the waveguide elements 34. For example, the acoustic energy that does not enter the core 37 of a waveguide element 34 can enter the cladding 40 of a waveguide element 34, or another material that is used to hold the waveguide elements 34 to each other. Energy that does not travel through the core material 37 can be absorbed, diffused and/or dissipated, where it will not be available to interfere with the primary energy pulse and echoes that travel within the acoustic waveguide fibers 34 (i.e. along the core material 37).

To cause the AWG 22 to produce an ultrasonic pulse, an electric field can be created between the electrodes 16, 19. This causes the piezoelectric film 13 to generate a pair of pulses 58, 61 of acoustic energy. The two pulses 58, 61 initially travel in different directions—a first one of the pulses 58 travels toward the first waveguide array 25 and a second one of the pulses 61 travels toward the second waveguide array 28. The second acoustic pulse 61, which contains no useful information about the target 31, arrives at the detector 55 and can be ignored by the acoustic detector array 55. The first acoustic pulse 58 travels through the first waveguide array 25 until it reaches the target object 31 or is reflected back by some other surface. The target object 31 can be the friction ridge surface of a finger. The reflected energy 64 travels back through the first waveguide array 25, passes through the two electrodes 16, 19 and the piezoelectric film 13, and then through the second waveguide array 28. The reflected pulse energy 64 provided by the second waveguide array 28 is then received by the detector 31, where the reflected pulse energy 64 can be converted to an electrical signal, such as a voltage signal, which can then be processed by electric circuits that monitor the acoustic detector array. The electric signal can be used to create an image of the object that reflected the energy.

Generally speaking, an ultrasonic fingerprint scanner can be a device which focuses ultrasound energy at a platen surface where a finger resides. At the ridges of the fingerprint, the skin is in contact with the platen. At the valleys of the fingerprint, air is in contact with the platen. Since the acoustic impedance of the platen is similar to the skin, ultrasound energy that reaches the ridge (skin) that is in contact with the platen will continue on into the finger and be dispersed. If, on the other hand, ultrasound energy reaches a valley where air contacts the platen, the energy will be reflected back and detected by the piezoelectric transducer. By examining individual locations on the platen, an image of the fingerprint can be created by mapping of the reflections, partial reflections and lack of reflections at every point on the platen.

Figure 5:
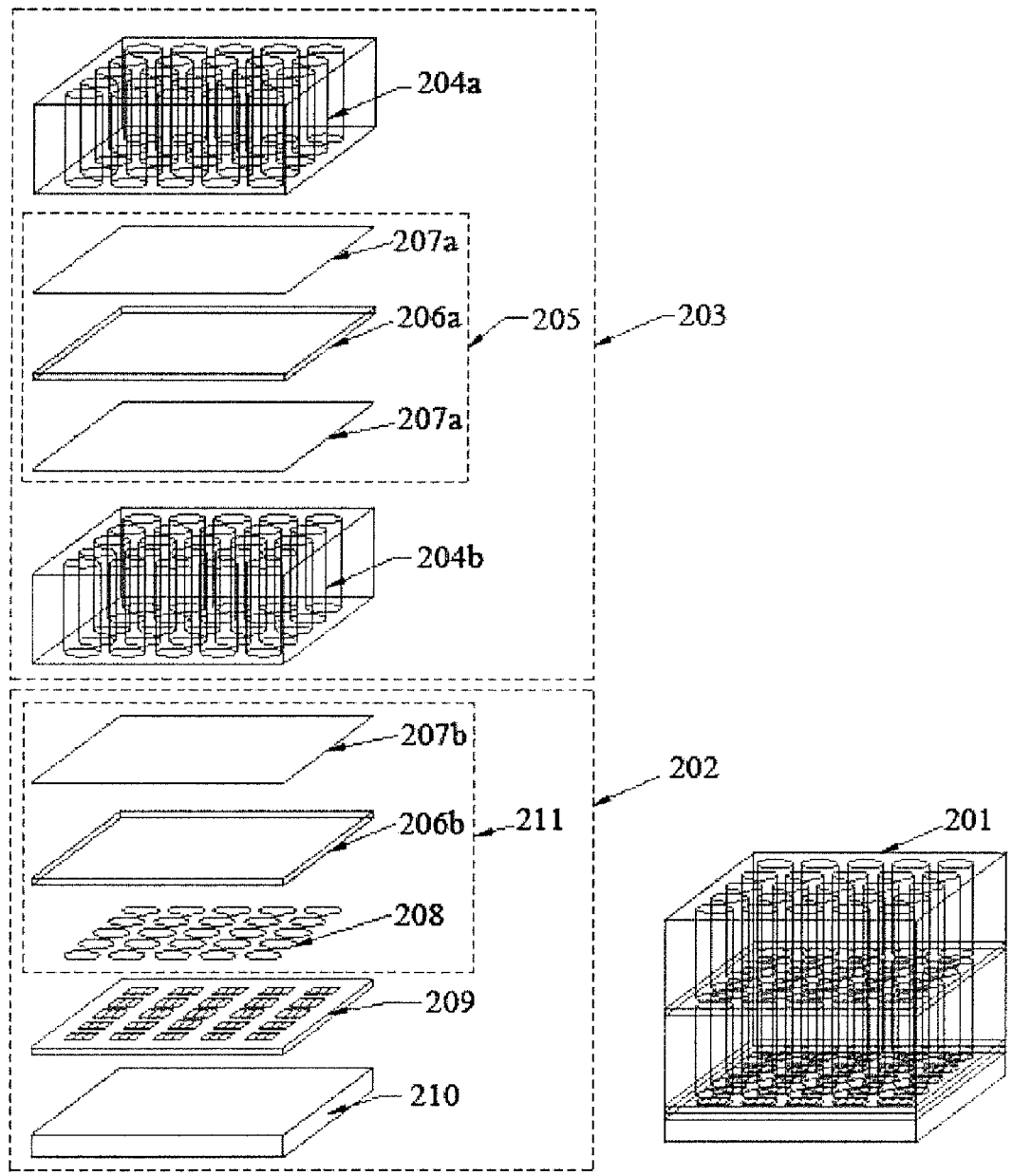
FIG. 5 is a diagram of an implementation of a fingerprint scanner using a piezoelectric array, a plane wave pulse generator and an acoustic fiber waveguide array to transfer acoustic energy to an ultrasonic detector array.

FIG. 5 is a diagram of an implementation of a fingerprint scanner 201 which is in keeping with the invention. In FIG. 5 there is shown an acoustic detector array 202 and an acoustic pulse array 203 as the two main subassemblies of its construction. The acoustic pulse array 203 can double as a fingerprint platen where a subject's finger can be placed for imaging. The acoustic detector array 202 is constructed with standard thin film transistor (TFT) techniques by applying a TFT array 209 onto a substrate 210, then applying an electrode array 208 that is in electrical contact to the inputs of the TFT array 209. Over the electrode array 208, a piezoelectric film 206b is applied and over-coated with a continuous electrode 207b. The assembly constitutes the acoustic detector array 202 and is sensitive to and will output signals in response to sonic pressure waves.

The acoustic pulse array 203 assembly is constructed by sandwiching a plane wave generator 205 between two coherent acoustic waveguide arrays 204a, 204b. The plane wave generator 205 is a piezoelectric film 206a which has had electrodes 207a applied to its opposite surfaces. The coherent acoustic waveguide arrays 204a, 204b can be constructed by filling a capillary array with a solid material whose acoustic shear velocity is less than that of the material of the capillary array construction. Typical materials of construction for this technique can be a glass capillary array filled with polystyrene (PS) or polymethylmethacrylate (PMMA) resin. The coherent acoustic waveguide arrays 204a, 204b also can be formed by fusing individual acoustic waveguide fibers so that their claddings form a continuous structure. Typical materials of construction for this method can be a polystyrene (PS) for the individual waveguide fibers in a polymethylmethacrylate (PMMA) matrix. Both methods lend themselves easily to construction techniques used to form fiber optic arrays.

When the acoustic detector array 202 and the acoustic pulse array 203 are brought together, the details of alignment must be dealt with so as to avoid Moiré patterning effects. This can be achieved by intentional misalignment of waveguides and detector pixels that differ in size or placement. For example, the electrodes of the electrode array 208 can be provided in a highly ordered arrangement. That is to say that the distances between adjacent electrodes are substantially the same, and the center-to-center distances between adjacent electrodes are substantially the same. When the electrodes of the electrode array 208 are provided in such a highly ordered arrangement, the waveguides 1 may be arranged in a manner that is not so ordered, and thus Moiré patterning effects can be avoided. For example, the waveguides 1 can be arranged in the detector array 204b so that the distances between adjacent waveguides 1 vary, and so that the center-to-center distances between adjacent waveguides 1 vary.

Another way of avoiding Moiré patterning effects is to arrange the waveguides 1 in the detector array 204b in a hexagonal-closest packed arrangement, and then positioning the detector array 204b so that the rows of waveguides 1 in the detector array 204b are offset by an angle of about five to ten degrees from the rows of electrodes in the electrode array 208.

Yet another way to avoid Moiré patterning effects is to arrange the waveguides 1 in the detector array 204b in a rectilinear pack arrangement, and then position the detector array 204b so that the rows of waveguides 1 in the detector array 204b are offset by an angle of about five to ten degrees from the rows of electrodes in the electrode array 208.

Regardless of whether a random arrangement, hexagonal-closest packed, or rectilinear pack arrangement is selected, we have found that Moiré patterning effects can be further reduced by selecting waveguides 1 having different diameters. We have found that by selecting waveguides 1 having diameters that vary by up to three percent, or even as high as five percent, is usually enough to avoid Moiré patterning effects.

It will be apparent to those versed in the art that the combination a plane wave generator 205, an acoustic detector array 202 and an acoustical optics device (here, the waveguide arrays 204a, 204b) that transfers the acoustic image of a biological object to the acoustic detector array 202 constitutes a device suitable for reading the acoustic image of the biological object, and that this device can function as a fingerprint reader.

Although the invention has been described in conjunction with a fingerprint scanner or reader, its use can be applied to other applications which seek to create an acoustic image of an object.

Having generally described the system depicted in FIG. 5, additional detail will now be provided. In FIG. 5 there is shown a biometric fingerprint scanner 201 where the platen that receives the finger for imaging is a surface of an acoustic pulse array 203 and the acoustic pulse array 203 is acoustically coupled to an ultrasonic detector array 202. The acoustic pulse array 203 can be constructed of a pair of coherent acoustic waveguide arrays 204a, 204b that have a plane wave generator 205 sandwiched between them. The plane wave generator 205 can be constructed of a piezoelectric film 206a and a pair of electrodes 207a that are in intimate contact with the opposite surfaces of the piezoelectric film 206a. And the acoustic waveguide arrays 204 can be constructed of materials differing in acoustic properties such that the individual waveguide elements have a lower material shear velocity than that of the matrix within which they are held.

The acoustic detector array 202 can be a semiconductor or TFT array of electronic pixel elements with the ability to be individually addressed by electronic control means. The semiconductor or TFT array can be affixed to an insulating substrate 202 for support and has an acoustic hydrophone array 211 intimately affixed to it so that the individual array elements of the acoustic detector array 202 are in electrical contact with the individual pixel element inputs. The acoustic detector array 202 can have a continuous electrode 207b on the surface away from the acoustic detector array 202 and an array of electrodes on the surface in contact with the detector array 202. Between the continuous electrode 207b and the electrode array 208 there can be a piezoelectric film 206b that generates the charge that is measured electronically by the detector array 202.

Although the present invention has been described with respect to one or more particular implementations, it will be understood that other implementations of the present invention can be made without departing from the spirit and scope of the present invention. Hence, the present invention is deemed limited only by the appended claims and the reasonable interpretation thereof.

What is claimed is:

1. A pulse array, comprising:
a first waveguide array; and
a second waveguide array; and
a plane wave pulse generator positioned between the first and second waveguide arrays and having a first side from which a first wave emanates, and a second side from which a second wave emanates.

2. The pulse array of claim 1, wherein the generator includes a piezoelectric film.

3. The pulse array of claim 2, wherein the generator includes an electrode substantially covering a side of the piezoelectric film.

4. The pulse array of claim 3, wherein the first waveguide array is attached to the electrode by an adhesive.

5. The pulse array of claim 2, wherein the generator includes a first electrode substantially covering a first side of the film, and a second electrode substantially covering a second side of the film.

6. The pulse array of claim 5, wherein the first waveguide array is attached to the first electrode, and the second waveguide array is attached to the second electrode.

7. The pulse array of claim 2, wherein the first waveguide array is oriented to transmit wave pulses from the generator in a direction that is substantially perpendicular to the piezoelectric film.

8. The pulse array of claim 1, wherein the first waveguide array is comprised of a plurality of waveguides, each waveguide having a core material and cladding material.

9. The pulse array of claim 8, wherein the cladding material of one waveguide has been fused with the cladding of another waveguide.

* * * * *